United States Patent
Hughett, Sr. et al.

(10) Patent No.: US 8,636,754 B2
(45) Date of Patent: Jan. 28, 2014

(54) CLIP APPLICATOR

(75) Inventors: James David Hughett, Sr., Liberty Township, OH (US); Matthew Monti, Cincinnati, OH (US); Adam Harp, Cincinnati, OH (US); Jason Iain Glithero, Mason, OH (US); Kenneth Lance Miller, Hamilton, OH (US); Philip P. Resig, Mason, OH (US); Salvatore Privitera, Mason, OH (US)

(73) Assignee: AtriCure, Inc., West Chester, OH (US)

( * ) Notice: Subject to any disclaimer, the term of this patent is extended or adjusted under 35 U.S.C. 154(b) by 696 days.

(21) Appl. No.: 12/944,430

(22) Filed: Nov. 11, 2010

(65) Prior Publication Data

US 2012/0123445 A1 May 17, 2012

(51) Int. Cl.
*A61B 17/08* (2006.01)

(52) U.S. Cl.
USPC .......................................................... 606/151

(58) Field of Classification Search
USPC .......................................... 24/455–456, 459
See application file for complete search history.

(56) References Cited

U.S. PATENT DOCUMENTS

| | | |
|---|---|---|
| 2,060,724 A | 11/1936 | Carroll |
| 2,371,978 A | 3/1945 | Perham |
| 3,032,039 A | 5/1962 | Beaty |
| 3,496,932 A | 2/1970 | Prisk et al. |
| 3,682,180 A | 8/1972 | McFarlane |
| 3,854,482 A | 12/1974 | Laugherty et al. |
| 3,856,016 A | 12/1974 | Davis |
| 3,856,017 A | 12/1974 | Perisse et al. |
| 3,856,018 A | 12/1974 | Perisse et al. |
| 3,954,108 A | 5/1976 | Davis |
| 4,226,239 A | 10/1980 | Polk et al. |
| 4,274,415 A | 6/1981 | Kanamoto et al. |
| 4,493,319 A | 1/1985 | Polk et al. |
| 4,552,128 A | 11/1985 | Haber |
| 4,788,966 A | 12/1988 | Yoon |
| 4,791,707 A | 12/1988 | Tucker |
| 4,869,268 A | 9/1989 | Yoon |
| 4,917,677 A | 4/1990 | McCarthy |
| 4,950,284 A | 8/1990 | Green et al. |
| 5,026,379 A | 6/1991 | Yoon |
| 5,100,416 A | 3/1992 | Oh et al. |
| 5,119,804 A | 6/1992 | Anstadt |

(Continued)

FOREIGN PATENT DOCUMENTS

| | | |
|---|---|---|
| EP | 1 600 108 A2 | 11/2007 |
| WO | WO 98/18389 | 5/1998 |

(Continued)

OTHER PUBLICATIONS

Unknown, Endowrist Instruments and Accessories Catalog, Intuitive Surgical, Sunnyvale, California, Sep. 2005.

(Continued)

*Primary Examiner* — Corrine M McDermott
*Assistant Examiner* — Son Dang
(74) *Attorney, Agent, or Firm* — Porter Wright Morris & Arthur LLP (57) ABSTRACT

A clamp assembly comprising: (a) a clamping device biased toward a closed position; (b) a first retainer bar removably coupled to the clamping device; (c) a second retainer bar removably coupled to the clamping device, where the first retainer bar and the second retainer bar are oriented in parallel to one another.

15 Claims, 5 Drawing Sheets

(56) References Cited

U.S. PATENT DOCUMENTS

| | | |
|---|---|---|
| 5,171,250 A | 12/1992 | Yoon |
| 5,217,030 A | 6/1993 | Yoon |
| 5,217,473 A | 6/1993 | Yoon |
| 5,258,000 A | 11/1993 | Gianturco |
| 5,282,829 A | 2/1994 | Hermes |
| 5,290,299 A | 3/1994 | Fain et al. |
| 5,306,234 A | 4/1994 | Johnson |
| 5,309,927 A | 5/1994 | Welch |
| 5,334,209 A | 8/1994 | Yoon |
| 5,336,252 A | 8/1994 | Cohen |
| 5,342,373 A | 8/1994 | Stefanchik et al. |
| 5,366,459 A | 11/1994 | Yoon |
| 5,425,740 A | 6/1995 | Hutchinson, Jr. |
| 5,439,156 A | 8/1995 | Grant et al. |
| 5,445,167 A | 8/1995 | Yoon et al. |
| 5,452,733 A | 9/1995 | Sterman et al. |
| 5,549,628 A | 8/1996 | Cooper et al. |
| 5,582,616 A | 12/1996 | Bolduc et al. |
| 5,609,599 A | 3/1997 | Levin |
| 5,620,452 A | 4/1997 | Yoon |
| 5,665,100 A | 9/1997 | Yoon |
| 5,667,518 A | 9/1997 | Pannell |
| 5,681,330 A | 10/1997 | Hughett et al. |
| 5,683,405 A | 11/1997 | Yacoubian et al. |
| 5,728,121 A | 3/1998 | Bimbo et al. |
| 5,758,420 A | 6/1998 | Schmidt et al. |
| 5,762,255 A | 6/1998 | Chrisman et al. |
| 5,782,397 A | 7/1998 | Koukline |
| 5,782,844 A | 7/1998 | Yoon et al. |
| 5,810,851 A | 9/1998 | Yoon |
| 5,810,882 A | 9/1998 | Bolduc et al. |
| 5,824,008 A | 10/1998 | Bolduc et al. |
| 5,830,221 A | 11/1998 | Stein et al. |
| 5,833,700 A | 11/1998 | Fogelberg et al. |
| 5,843,121 A | 12/1998 | Yoon |
| 5,865,791 A | 2/1999 | Whayne et al. |
| 5,893,863 A | 4/1999 | Yoon |
| 5,919,202 A | 7/1999 | Yoon |
| 5,921,997 A | 7/1999 | Fogelberg et al. |
| 5,922,001 A | 7/1999 | Yoon |
| 5,922,002 A | 7/1999 | Yoon |
| 5,964,772 A | 10/1999 | Bolduc et al. |
| 5,984,917 A | 11/1999 | Fleischman et al. |
| 5,984,938 A | 11/1999 | Yoon |
| 5,984,939 A | 11/1999 | Yoon |
| 6,042,563 A | 3/2000 | Morejohn et al. |
| 6,074,418 A | 6/2000 | Buchanan et al. |
| 6,088,889 A | 7/2000 | Luther et al. |
| 6,096,052 A | 8/2000 | Callister et al. |
| 6,099,550 A | 8/2000 | Yoon |
| 6,152,144 A | 11/2000 | Lesh et al. |
| 6,165,183 A | 12/2000 | Kuehn et al. |
| 6,231,561 B1 | 5/2001 | Frazier et al. |
| 6,270,516 B1 | 8/2001 | Tanner et al. |
| 6,280,415 B1 | 8/2001 | Johnson |
| 6,290,674 B1 | 9/2001 | Roue et al. |
| 6,296,656 B1 | 10/2001 | Bolduc et al. |
| 6,299,612 B1 | 10/2001 | Ouchi |
| 6,312,447 B1 | 11/2001 | Grimes |
| 6,330,964 B1 | 12/2001 | Kayan et al. |
| 6,387,105 B1 | 5/2002 | Gifford, III et al. |
| 6,402,765 B1 | 6/2002 | Monassevitch et al. |
| 6,416,554 B1 | 7/2002 | Alferness et al. |
| 6,428,548 B1 | 8/2002 | Durgin et al. |
| 6,436,088 B2 | 8/2002 | Frazier et al. |
| 6,447,542 B1 | 9/2002 | Weadock |
| 6,450,391 B1 | 9/2002 | Kayan et al. |
| 6,465,196 B1 | 10/2002 | Hobbs et al. |
| 6,485,407 B2 | 11/2002 | Alferness et al. |
| 6,488,689 B1 | 12/2002 | Kaplan et al. |
| 6,491,701 B2 | 12/2002 | Tierney et al. |
| 6,491,706 B1 | 12/2002 | Alferness et al. |
| 6,506,149 B2 | 1/2003 | Peng et al. |
| 6,508,829 B1 | 1/2003 | Levinson et al. |
| 6,514,265 B2 | 2/2003 | Ho et al. |
| 6,578,585 B1 | 6/2003 | Stachowski et al. |
| 6,579,304 B1 | 6/2003 | Hart et al. |
| 6,584,360 B2 | 6/2003 | Francischelli et al. |
| 6,607,504 B2 | 8/2003 | Haarala et al. |
| 6,607,542 B1 | 8/2003 | Wild |
| 6,610,074 B2 | 8/2003 | Santilli |
| 6,652,515 B1 | 11/2003 | Maguire et al. |
| 6,676,684 B1 | 1/2004 | Morley et al. |
| 6,746,461 B2 | 6/2004 | Fry |
| 6,770,081 B1 | 8/2004 | Cooper et al. |
| 6,793,664 B2 | 9/2004 | Mazzocchi et al. |
| 6,849,075 B2 | 2/2005 | Bertolero et al. |
| 6,849,078 B2 | 2/2005 | Durgin et al. |
| 6,872,210 B2 * | 3/2005 | Hearn ............................ 606/71 |
| 6,896,684 B2 | 5/2005 | Monassevitch et al. |
| 6,911,032 B2 | 6/2005 | Jugenheimer et al. |
| 7,008,401 B2 | 3/2006 | Thompson et al. |
| 7,113,831 B2 | 9/2006 | Hooven |
| 7,118,582 B1 | 10/2006 | Wang et al. |
| 7,169,164 B2 | 1/2007 | Borillo et al. |
| 7,226,458 B2 | 6/2007 | Kaplan et al. |
| 7,318,829 B2 | 1/2008 | Kaplan et al. |
| 7,344,543 B2 | 3/2008 | Sra |
| 2001/0005787 A1 | 6/2001 | Oz et al. |
| 2001/0039434 A1 | 11/2001 | Frazier et al. |
| 2001/0039435 A1 | 11/2001 | Roue et al. |
| 2002/0013605 A1 | 1/2002 | Bolduc et al. |
| 2002/0022860 A1 | 2/2002 | Borillo et al. |
| 2002/0026214 A1 | 2/2002 | Tanner |
| 2002/0026216 A1 | 2/2002 | Grimes |
| 2002/0032454 A1 | 3/2002 | Durgin et al. |
| 2002/0035374 A1 | 3/2002 | Borillo et al. |
| 2002/0049457 A1 | 4/2002 | Kaplan et al. |
| 2002/0055750 A1 | 5/2002 | Durgin et al. |
| 2002/0058967 A1 | 5/2002 | Jervis |
| 2002/0062130 A1 | 5/2002 | Jugenheimer et al. |
| 2002/0065524 A1 | 5/2002 | Miller et al. |
| 2002/0077660 A1 | 6/2002 | Kayan et al. |
| 2002/0099390 A1 | 7/2002 | Kaplan et al. |
| 2002/0103492 A1 | 8/2002 | Kaplan et al. |
| 2002/0111637 A1 | 8/2002 | Kaplan et al. |
| 2002/0111641 A1 | 8/2002 | Peterson et al. |
| 2002/0111647 A1 | 8/2002 | Khairkhahan et al. |
| 2002/0169377 A1 | 11/2002 | Khairkhahan et al. |
| 2002/0177859 A1 | 11/2002 | Monassevitch et al. |
| 2002/0177862 A1 | 11/2002 | Aranyi et al. |
| 2003/0009441 A1 | 1/2003 | Holsten et al. |
| 2003/0018362 A1 | 1/2003 | Fellows et al. |
| 2003/0023248 A1 | 1/2003 | Parodi |
| 2003/0023266 A1 | 1/2003 | Borillo et al. |
| 2003/0055422 A1 | 3/2003 | Lesh |
| 2003/0158464 A1 | 8/2003 | Bertolero |
| 2004/0030335 A1 | 2/2004 | Zenati et al. |
| 2004/0064138 A1 | 4/2004 | Grabek |
| 2004/0073241 A1 | 4/2004 | Barry et al. |
| 2004/0097982 A1 | 5/2004 | Jugenheimer et al. |
| 2004/0215216 A1 | 10/2004 | Gannoe et al. |
| 2005/0085808 A1 | 4/2005 | Nakao |
| 2005/0149068 A1 | 7/2005 | Williams et al. |
| 2005/0149069 A1 | 7/2005 | Bertolero et al. |
| 2005/0203561 A1 | 9/2005 | Palmer et al. |
| 2006/0020271 A1 | 1/2006 | Stewart et al. |
| 2006/0084974 A1 | 4/2006 | Privitera et al. |
| 2006/0161147 A1 | 7/2006 | Privitera et al. |
| 2006/0161149 A1 | 7/2006 | Privitera et al. |
| 2007/0149988 A1 | 6/2007 | Michler et al. |
| 2008/0033457 A1 | 2/2008 | Francischelli et al. |
| 2008/0125795 A1 | 5/2008 | Kaplan et al. |
| 2009/0012545 A1 | 1/2009 | Williamson, IV et al. |
| 2010/0004663 A1 | 1/2010 | Murphy et al. |
| 2010/0204716 A1 | 8/2010 | Stewart et al. |
| 2011/0152922 A1 | 6/2011 | Jeong |
| 2012/0035622 A1 | 2/2012 | Kiser et al. |

FOREIGN PATENT DOCUMENTS

| | | |
|---|---|---|
| WO | WO 99/62409 A1 | 12/1999 |
| WO | WO 01/35832 A2 | 5/2001 |
| WO | WO 01/97696 | 12/2001 |

(56) References Cited

FOREIGN PATENT DOCUMENTS

| | | |
|---|---|---|
| WO | WO 03/011150 A1 | 2/2003 |
| WO | WO 03/096881 | 11/2003 |
| WO | WO 2007/009099 A2 | 1/2007 |
| WO | PCT/US2006/027553 | 1/2008 |
| WO | PCT/US2012/051002 | 10/2012 |

OTHER PUBLICATIONS

Kamohara et al, Impact of left atrial appendage exclusion on left atrial function, J Thorac Cardiov Surg 2007;133:174-81,© 2007 American Association for Thoracic Surgery, USA.

Fumoto et al, A novel device for left atrial appendage exclusion: The third-generation atrial exclusion device, J Thorac Cardiov Surg 2008;136:1019-27, © 2008 American Association for Thoracic Surgery, USA.

Lipkin et al, Aneurysmal dilation of left atrial appendage diagnosed by cross sectional echocardiography and surgically removed, Br Heart J 1985; 53:69-71, National Heart Hospital, London, UK.

Cohn et al, Right thoracotomy, femorofemoral bypass, and deep hypothermia for re-replacement of the mitral valve, Ann Thorac Surg 1989;48:69-71, © 1989 Society of Thoracic Surgeons, USA.

Al-Saady et al, Left atrial appendage: structure, function, and role in thrombo-boembolism, Heart 1999;82:547-555, St. George's Hosp Med School, London UK.

Kaymaz et al, Location, Size and Morphological Characteristics of Left Atrial Thrombi as Assessed by Echocardiography in Patients with Rheumatic Mitral Valve Disease, Eur. J Echocardiography, vol. 2, Issue 4, Dec. 2001, pp. 270-276, © 2001 The European Society of Cardiology.

Rosenzweig et al, Thromboembolus from a Ligated Left Atrial Appendage, J Am Soc Echocardiography, vol. 14, pp. 396-398, May 2001, © 2001 American Society of Echocardiography, USA.

Hondo et al, The Role of the Left Atrial Appendage; A Volume Loading Study in Open-chest Dogs, Jpn Heart J, Mar. 1995, pp. 225-234, Japan.

Veinot et al, Anatomy of the Normal Left Atrial Appendage: A Quantitative Study of Age-Related Changes . . . , ahajournals 1997; 96: 3112-3115, USA.

Halperin et al, Obliteration of the Left Atrial Appendage for Prevention of Thromboembolis, J Am Coll of Cardiol, 2003;42:1259-1261, USA.

Unknown, Transesophageal Echocardiographic Correlates of Thromboembolism in High Risk Patients with Nonvalvular Atrial Fibrillation, The American College of Physicians, Apr. 1998, pp. 639-647, © 1998 American College of Physicians, USA.

Omari et al, Effect of right atrial appendectomy on the release of atrial natriuretic hormone, J Thorac Cardiovasc Surg 1991; 102:272-279, USA.

Mole et al, Desmoid Tumour in Thoractomy Scar 5 Years After Excision of a Left Giant Atrial Appendage Aneurysm in Female with a Family History of Gardner's Syndrome, Thorac Cardiovasc Surg 40 (1991) pp. 300-302, © 1992 Georg Thieme Verlag Stuttgart, New York.

Crystal et al, Left Atrial Appendage Occlusion Study (LAAOS): A randomized clinical trial of left atrial appendage occlusion during routine coronary artery bypass graft surgery for long-term stroke prevention, Am Heart J 2003; 145:174-178, © 2003 Mosby, Inc., USA.

Garcia-Fernadez et al, Role of left atrial appendage obliteration in stroke reduction in patients with mitral valve prosthesis: A transeophageal echocardiographic study, J Am Coll Cardiol 2003;42:1253-1258, © 2003 American College of Cardiology Foundation, USA.

Burke et al, Improved Surgical Approach to Left Atrial Appendage Aneurysm, J Cardi Surg, 1992, vol. 7, No. 2, pp. 104-107, USA.

Fisher et al, Large Gradient Across a Partially Ligated Left Atrial Appendage, J Am Soc Echocardiography, vol. 11, No. 12, pp. 1163-1165, © 1998 American Society of Echocardiography, USA.

Grundeman et al, Experimental videothoracoscopic cannulation of the left atrial appendix, Surg Endosc (1993) 7:511-513, © 1993 Springer-Verlag New York, Inc., USA.

Lynch et al, Recanalization of the Left Atrial Appendage Demonstrated by Transesophageal Echocardiography, Ann Torac Surg, 1997; 63:1774-5, Published by Elsevier Science Inc., © 1997 The Society of Thoracic Surgeons, USA.

Hoit et al, Altered Left Atrial Compliance After Atrial Appendectomy, AHA Circulation Research, vol. 72, No. 1, Jan. 1993, pp. 167-175, From University of Cincinnati Medical Center, Department of Internal Medicine, Cincinnati, Ohio, USA.

Landymore, et al, Staple Closure of the Left Atrial Appendage, The Canadian Journal of Surgery, vol. 27, No. 2, Mar. 1984, pp. 144-145, From Victoria General Hospital, Dept. of Surgery,Div. of Cardiovascular Surgery, Halifax, NS.

Robin et al, Strangulation of the Left Atrial Appendage through a Congenital Partial Pericardial Defect, CHEST, 67:3, Mar. 1975, pp. 354-355, From Dept. of Cariology, Hutzel Hospital Medical Unit, Wayne State University, Detroit, MI, USA.

Tabata, et al, Role of Left Atrial Appendage in Left Atrial Reservoir Function as Evaluated by Left Atrial Appendage Clamping During Cardiac Surgery, American Journal of Cardiology, vol. 81, Feb. 1, 1998, pp. 327-332, © 1998 Excerpta Medica, Inc., USA.

Aytac, et al, Intrapericardial aneurysm of the left atrial appendix, J. Cardiovas. Surg., 21, 1980, pp. 509-511, USA.

Lindsay, M.D., Bruce D., Obliteration of the Left Atrial Appendage: A Concept Worth Testing, Ann Thorac Surg 1996;61:515, © 1996 The of Society Thoracic Surgeons, Published by Elsevier Science, Inc. ,USA.

Landymore, M.D., R. W., Stapling of Left Atrial Appendage, To the Editor: , Ann Thorac Surg 1989;47:794,© 1989 The Society of Thoracic Surgeons, USA.

Disesa, et al, Ligation of the Left Atrial Appendage Using an Automatic Surgical Stapler, Accepted for publication Jul. 26, 1988, Div. of Cardiac Surgery, Brigham and Women's Hospital, Boston, MA.

Wakabayashi, MD., Akio, Expanded applications of diagnostic and therapeutic thoracoscopy, J. Thorac Cardiovasc Surg 1991;102:721-3, from Dept. of Surgery, University of Californaia, Irvine, Irvine, CA.

Thomas, TV, Left atrial appendage and valve replacement, Am Heart Journal, vol. 84, No. 6, Dec. 1972, pp. 838-839, USA.

Coselli, et al, Congenital Intrapericardial Aneurysmal Dilatation of the Left Atrial Appendage, Case Reports: The Annals of Thoracic Surgery, vol. 39, No. 5, May 1985, pp. 466-468, From Dept. of Surgery, Baylor College of Medicine, Houston TX.

Coffin, M.D., Laurence H., Use of the Surgical Stapler to Obliterate the Left Atrial Appendage, Surgery, Gynecology & Obsterics, Jun. 1985, vol. 160, pp. 565-566, From Div., of Thoracic and Cardiac Surgery, Univ of Vermont College of Medicine, Burlington, VT.

Katz, et al, Surgical Left Atrial Appendage Ligation Is Frequently Incomplete: A Transesophageal Echocardiographic Study, J Am College of Cardiology, vol. 36, No. 2, Aug. 2000, © 2000 American College of Cardiology, Published by Elsevier Science, Inc., USA.

Ganeshakrishnan, et al, Congenital Intrapericardial Aneurysm of the Left-Atrial Appendage, Case Report: Thorac. cardiovasc. Surgeon 40 (1992), 382-384, © Georg Thieme Verlag Stuttgart, New York, USA.

Unknown, surgical procedure report to track prior art with regards to a minimimally invasive left atrial appendage exclusion, Jan. 1, 2007, USA.

Stollberger, et al, Elimination of the Left Atrial Appendage to Prevent Stroke or Embolism?, Opinions/Hypotheses, CHEST/ 124 / 6/ Dec. 2003, pp. 2356-2362, © American College of Chest Physicians, USA.

Cox, et al, Five-Year Experience with the Maze Procedure for Atrial Fibrillation, Ann Thorac Surg 1993; 56:814-24, Presented at the Twenty-ninth Annual Meeting of The Society of Thoracic Surgeons, San Antonio, TX, Jan. 25-27, 1993, © 1993 The Society of Thoracic Surgeons, USA.

Stollberger, et al, Is left atrial appendage occlusion useful for prevention of stroke or embolism in atrial fibrillation?, Z Kardiol 91:376-379 (2002), © Steinkopff Verlag 2002, Germany.

Riley, et al, Mitral Valve Repair, CTSNET Experts' Techniques, doc 5729, pp. 1-7, © 2004 Cardiothoracic Surgery Network, USA.

(56) References Cited

OTHER PUBLICATIONS

Johnson, et al, The left atrial appendage: our most lethal human attachment! Surgical implications, EU J Cardio-thor Surg 17 (2000) 718-722, Presented at the 13th Annual Meeting of The European Association for Cardio-thoracic Surgery, Glasgow, Scotland, UK, Sep. 5-8, 1999, © 2000 Elsevier Science B.V.

Blackshear, et al, Thoracoscopic Extracardiac Obliteration of the Left Atrial Appendage for Stroke Risk Reduction in Atrial Fibrillation, JACC, vol. 42, No. 7, Oct. 1, 2003:1249-52, © 2003 American College of Cardiology Foundation, Published by Elsevier Inc., USA.

Odell, et al, Thoracoscopic Obliteration of the Left Atrial Appendage: Potential for Stroke Reduction?, Ann Thorac Surg 1996;61:565-9, © 1996 The Society of Thoracic Surgeons, Published by Elsevier Science Inc., USA.

Blackshear, et al, Appendage Obliteration to Reduce Stroke in Cardiac Surgical Patients with Atrial Fibrillation, Ann Thorac Surg 1996;61:755-9, © 1996 The Society of Thoracic Surgeons, Published by Elsevier Science Inc., USA.

Gillinov, et al, Stapled excision of the left atrial appendage, J Thorac Cardiovasc Surg 2005;129:679-80, © 2005 The American Association for Thoracic Surgery, USA.

Stollberger, et al, Stroke Prevention By Means of Left Atrial Appendage Strangulation?, To the Editor:, J Thorac Cardiovasc Surg 2010, p. 732, USA.

Kamohara et al, Evaluation of a novel device for left atrial appendage exclusion: The second-generation atrial exclusion device, J Thorac Cardiov Surg 2006;132:340-46, © 2006 American Association for Thoracic Surgery, USA.

Kamohara et al, A novel device for left atrial appendage exclusion, J Thorac Cardiov Surg 2005;130:1639-44, © 2005 American Association for Thoracic Surgery, USA.

Stollberger et al, Leave the left atrial appendage untouched for stroke prevention!, To the Editor:, J Thorac Cardiov Surg, vol. 134, No. 2, Aug. 2007, pp. 549-550, © 2007 American Association for Thoracic Surgery, USA.

Wudel et al, Video-Assisted Epicardial Ablation and Left Atrial Appendage Exclusion for Atrial Fibrillation: Extended Follow-up, Ann Thorac Surg, 2007.08.014, pp. 1-5, © 2007 The Society of Thoracic Surgeons, Published by Elsevier Inc., USA.

Salzberg, et al, Surgical left atrial appendage occulsion: evaluation of a novel device with magnetic resonance imaging, EU J Cardio-thor Surg 34 (2008) 766-770, © 2008 European Association for Cardio-Thoracic Surgery, Published by Elsevier B.V.

Salzberg, et al, Left atrial appendage clip occlusion: Early clinical results, J Thorac Cardiov Surg, vol. 139, No. 5, pp. 1269-1274, © 2010 The American Association for Thoracic Surgery, USA.

* cited by examiner

CLIP APPLICATOR

RELATED ART

Field of the Invention

The present invention is directed to applicators for clamps and, more specifically, for applicators that may be utilized in minimally invasive procedures to position and apply the occlusion clamps.

INTRODUCTION TO THE INVENTION

It is a first aspect of the present invention to provide a removable deployment device for a clamp comprising: (a) a first retainer bar including a line coupled thereto; (b) a second retainer bar including a second line coupled thereto, where the first retainer bar is coupled to the second retainer bar.

In a more detailed embodiment of the first aspect, the first retainer bar includes a first depression on its exterior surface, and the first line extends across the first depression. In yet another more detailed embodiment, the second retainer bar includes a second depression on its exterior surface, and the second line extends across the second depression. In a further detailed embodiment, the first retainer bar includes a projection extending therefrom, the projection including a crucifix. In still a further detailed embodiment, the second retainer bar includes a projection extending therefrom, the projection including a first segment extending perpendicularly from the second retainer bar, and a second segment including a hook mounted to the first segment.

In yet another more detailed embodiment of the first aspect, the second retainer bar includes a projection extending therefrom, the projection including a hook. In yet another more detailed embodiment of the first aspect, the engagement feature may be a hole into or through one or both retaining bars. In still another more detailed embodiment, the first retainer bar includes a first through hole, the second retainer bar includes a second through hole, and a third line is concurrently received within the first through hole and the second through hole to couple the first and second retainer bars. In a further detailed embodiment, an extraction tab is coupled to the third line. In still a further detailed embodiment, at least one of the first line, the second line, and the third line comprises a suture. In a more detailed embodiment, the first line comprises a first suture, the second line comprises a second suture, and the third line comprises a third suture.

It is a second aspect of the present invention to provide a clamp assembly comprising: (a) a clamp including at least first and second elongate clamping portions biased toward one another; (b) a first retainer bar including a first line removably coupling the first retainer bar to the first elongate clamping portion; (c) a second retainer bar including a second line removably coupling the second retainer bar to the second elongate clamping portion, where the first retainer bar is coupled to the second retainer bar.

In a more detailed embodiment of the second aspect, the first retainer bar includes a first depression on its exterior surface, and the first line extends across the first depression. In yet another more detailed embodiment, the second retainer bar includes a second depression on its exterior surface, and the second line extends across the second depression. In a further detailed embodiment, the first retainer bar includes a projection extending therefrom, the projection including a crucifix. In still a further detailed embodiment, the second retainer bar includes a projection extending therefrom, the projection including a first segment extending perpendicularly from the second retainer bar, and a second segment including a hook mounted to the first segment. In a more detailed embodiment, the second retainer bar includes a projection extending therefrom, the projection including a hook.

In yet another more detailed embodiment of the second aspect, the first retainer bar includes a first through hole, the second retainer bar includes a second through hole, and the third line is concurrently received within the first through hole and the second through hole. In still another more detailed embodiment, an extraction tab is coupled to the first and second retainer bars. In a further detailed embodiment, at least one of the first line, the second line, and the third line comprises a suture. In still a further detailed embodiment, the first line comprises a first suture, the second line comprises a second suture, and the third line comprises a third suture. In a more detailed embodiment, the clamp comprises a first and second elongate clamping portions respectively having ends coupled together with respective resilient urging members configured to urge the first and second elongate clamping portions toward one another. In a more detailed embodiment, the clamp further comprises a fabric covering over the first and second elongate clamping portions.

It is a third aspect of the present invention to provide a method of fabricating a clamp comprising: (a) mounting a first retainer bar to a first elongate clamping portion of a clamp using a first line, the clamp also including a second elongate clamping portion, where the first and second elongate clamping portions are biased toward one another; (b) mounting a second retainer bar to the second elongate clamping portion of the clamp using a second line; (c) mounting the first retainer bar to the second retainer bar, where the first and second elongate clamping portions each include proximal and distal longitudinal ends, where the proximal longitudinal ends are coupled to a first spring, and where the distal longitudinal ends are coupled to a second spring.

In a more detailed embodiment of the third aspect, the first line comprises a suture. In yet another more detailed embodiment, mounting the first retainer bar to the first elongate clamping portion includes looping the first line around the first elongate clamping portion and tying the first line to the first retainer bar, and mounting the second retainer bar to the second elongate clamping portion includes looping the second line around the second elongate clamping portion and tying the second line to the second retainer bar. In a further detailed embodiment, tying the first line to the first retainer bar includes forming a plurality of half hitch knots, and tying the second line to the second retainer bar includes forming; a plurality of half hitch knots. In still a further detailed embodiment, tying the first line to the first retainer bar includes forming a timberline knot, and tying the second line to the second retainer bar includes forming a timberline knot. In a more detailed embodiment, mounting the first retainer bar to the second retainer bar includes using a third line coupled to both the first retainer bar and the second retainer bar. In a more detailed embodiment, the first elongate clamping portion and the second elongate clamping portion are coupled together using at least one line. In a more detailed embodiment, at least one of the first retainer bar and the second retainer bar includes a crucifix projection adapted to be gripped by endoscopic graspers. In another more detailed embodiment, the first retainer bar includes a first projection adapted to be gripped by endoscopic graspers, where the first projection is directed away from the clamp, and the second retainer bar includes a second projection adapted to be gripped by endoscopic graspers, where the second projection is directed away from the clamp. The endoscopic graspers may be manual or robotically driven.

It is a fourth aspect of the present invention to provide a clamp assembly comprising: (a) a clamping device biased toward a closed position; (b) a first retainer bar removably coupled to the clamping device; (c) a second retainer bar removably coupled to the clamping device, where the first retainer bar and the second retainer bar are oriented in parallel to one another and, where the first retainer bar and the second retainer bar each include an engagement feature to facilitate grasping by a grasping device.

In a more detailed embodiment of the fourth aspect, the first retainer bar includes a first depression on its exterior surface, the first retainer bar includes a first line removably coupling the first retainer bar to the clamping device and, the first line extends across the first depression. In yet another more detailed embodiment, the second retainer bar includes a second depression on its exterior surface, the second retainer bar includes a second line removably coupling the second retainer bar to the clamping device and, the second line extends across the second depression. In a further detailed embodiment, the first retainer bar includes a projection extending therefrom, the projection including a crucifix. In still a further detailed embodiment, the second retainer bar includes a projection extending therefrom, the projection including a first segment extending perpendicularly from the second retainer bar, and a second segment including a hook mounted to the first segment. In a more detailed embodiment, the second retainer bar includes a projection extending therefrom, the projection including a hook.

In yet another more detailed embodiment of the fourth aspect, the first retainer bar includes a first through hole, the second retainer bar includes a second through hole and, a line is concurrently received within the first through hole and the second through hole. In still another more detailed embodiment, the clamp assembly includes an extraction tab coupled to the line. In a further detailed embodiment, at least one of the first retainer bar and the second retainer bar is removably coupled to the clamping device using a suture. In still a further detailed embodiment, the first retainer bar is removably coupled to the clamping device using a first suture and, the second retainer bar is removably coupled to the clamping device using a second suture. In a more detailed embodiment, the clamping device comprises a first and second elongate clamping portions respectively having ends coupled together with respective resilient urging members configured to urge the first and second elongate clamping portions toward one another. In a more detailed embodiment, the clamping device further comprises a fabric covering over the first and second elongate clamping portions.

It is a fifth aspect of the present invention to provide a clamp assembly comprising: (a) a clamping device biased toward a closed position; (b) a first retainer bar removably coupled to the clamping device; (c) a second retainer bar removably coupled to the clamping device and, where the first retainer bar and the second retainer bar are oriented in parallel to one another.

In a more detailed embodiment of the fifth aspect, at least one of the first retainer bar and the second retainer bar includes a line to removably couple at least one of the first retainer bar and the second retainer bar to the clamping device. In yet another more detailed embodiment, the line lies across a cutting zone. In a further detailed embodiment, the cutting zone comprises a depression formed within an exterior of the least one of the first retainer bar and the second retainer bar. In still a further detailed embodiment, the line comprises at least one of a suture, a cable, a strap, and a thread. In a more detailed embodiment, at least one of the engagement features includes a projection. In more detailed embodiment, the projection comprises at least one of a cruciform and a hook. In another more detailed embodiment, each engagement feature includes a projection and, the projection of the first retainer bar is different from the projection of the second retainer bar. In yet another more detailed embodiment, at least one of the engagement features includes a through hole. In still another more detailed embodiment, the engagement feature of the first retainer bar includes a through hole and, the engagement feature of the second retainer bar includes a through hole.

In yet another more detailed embodiment of the fifth aspect, the first retainer bar is coupled to the second retainer bar using a retainer. In still another more detailed embodiment, the retainer comprises a line. In a further detailed embodiment, the line comprises at least one of a suture and a cable. In still a further detailed embodiment, the first retainer bar and the second retainer bar each include an engagement feature to facilitate grasping by a grasping device. In a more detailed embodiment, at least one of the first retainer bar and the second retainer bar includes a line to retrieve the retainer bar post decoupling at least one of the first retainer bar and the second retainer bar from the clamping device. In a more detailed embodiment, the clamping device comprises a first and second elongate clamping portions respectively having ends coupled together with respective resilient urging members configured to urge the first and second elongate clamping portions toward one another. In another more detailed embodiment, the clamping device further comprises a fabric covering over the first and second elongate clamping portions. In yet another more detailed embodiment, the clamping assembly further comprises at least one limiting line coupled to the clamping device, wherein the clamping device comprises a first and second elongate clamping portions configured to move toward and away from one another, the at least one limiting line limiting how far the first and second elongate clamping portions can move away from one another. In still another more detailed embodiment, the at least one limiting line is coupled to the first and second retainer bars. In still a further more detailed embodiment, the at least one limiting line is coupled to the first and second elongate clamping portions. In yet a further more detailed embodiment, the at least one limiting line is further coupled to the clamping device to continue the coupling of the at least one limiting line with the first and second elongate clamping portions.

As used herein, the term "line" means or includes a tether such as, without limitation, a cable, a string, a thread, and/or a suture.

As used herein, the term "grasper" means any device capable of grasping or gripping and includes, without limitation, endowrist jawed devices such as endoscopic graspers, minimally invasive graspers, tongs, and forceps.

DETAILED DESCRIPTION

The exemplary embodiments of the present invention are described and illustrated below to encompass methods and devices for opening and closing clamps/clips such as, without limitation, occlusion clamps. Of course, it will be apparent to those of ordinary skill in the art that the embodiments discussed below are exemplary in nature and may be reconfigured without departing from the scope and spirit of the present invention. However, for clarity and precision, the exemplary embodiments as discussed below may include optional steps, methods, and features that one of ordinary skill should recognize as not being a requisite to fall within the scope of the present invention.

Referencing FIGS. 1-5, an exemplary occlusion clamp 100, as shown and described in U.S. patent application Ser. No. 11/994,725, filed on Jul. 8, 2008, the disclosure of which is incorporated herein by reference, includes an applicator assembly 102 in order to reposition and deploy the occlusion clamp. The exemplary applicator assembly 102 includes a pair of retainer bars 104, 106 mounted to a fabric cover material 108 using sutures 110, 112. In this exemplary embodiment, the fabric cover material 108 may be made of a material such as polyester having been sewn around the clamping portions 114, 116 and the urging members 118, 120.

Each retainer bar 104, 106 includes complementary depressions 122, 124 formed into the circumferential surface on opposite sides at two different longitudinal locations. Two primary through holes 126, 128 are longitudinally outset from each set of depressions 122, 124 and extend perpendicularly through the bar 104, 106. The bars 104, 106 can contain more or less than two through holes. These primary through holes 126, 128 are also centered from side to side with respect to the diameter of the retainer bars 104, 106 so that the central axis of each hole intersects the central, longitudinal axis of the retainer bar. More specifically, each primary through hole 126, 128 includes complementary top and bottom openings that are on the same sides as the depressions 122, 124. In other words, the rounded sides of the retainer bars 104, 106 that are offset approximately ninety degrees from the depressions 122, 124 are also offset approximately 90 degrees from the top and bottom openings of each primary through hole 126, 128. Inset from the ends 130 of each retainer bar 104, 106 are secondary through holes 132 extending perpendicularly through the bar and are centered from side to side. But these secondary through holes 132 are perpendicular with respect to, but do not intersect, the primary through holes 126, 128. As with the primary through holes 126, 128, the secondary through holes 132 also have opposed top and bottom openings. As will be discussed in more detail below, the holes 126, 128 accommodate sutures 110, 112 to couple the bars 104, 106 to the occlusion clamp 100.

Figure 1:
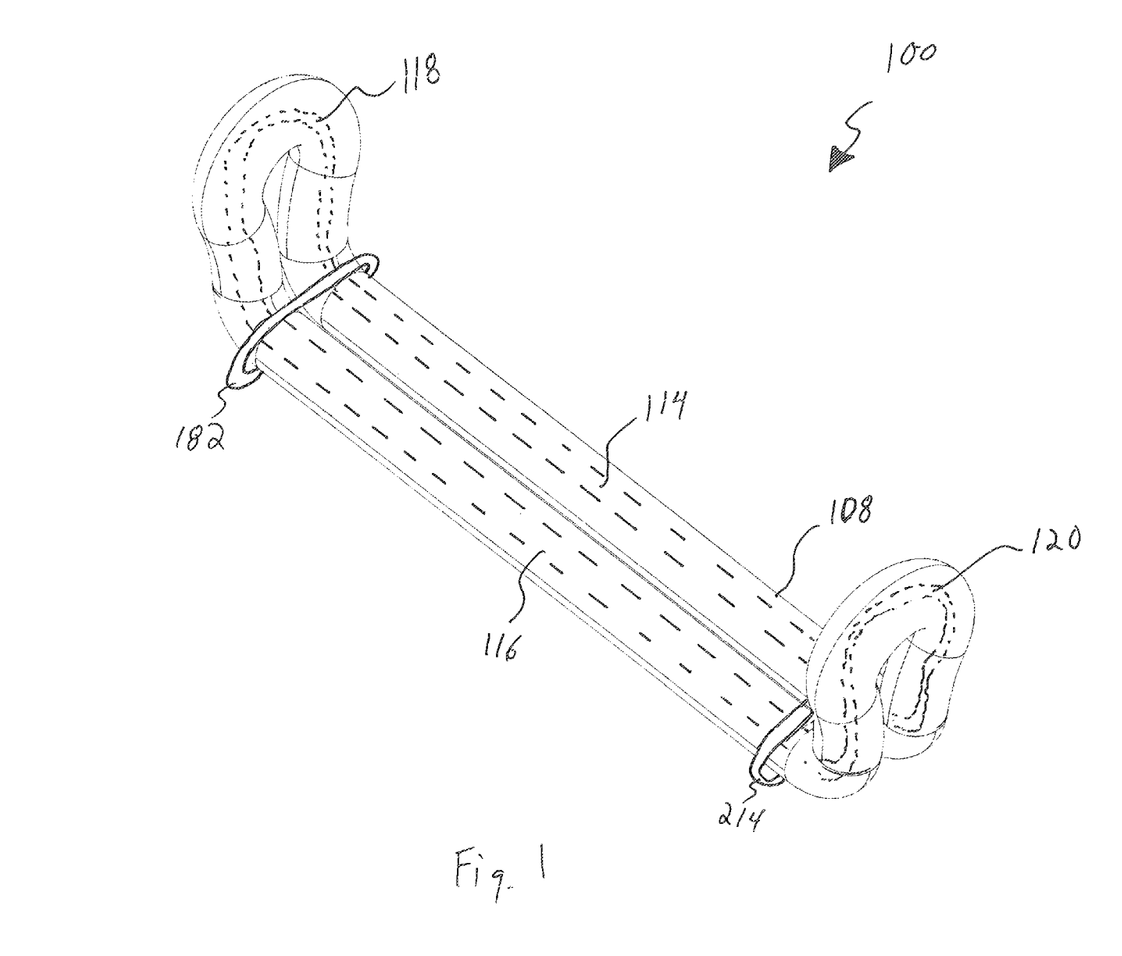
FIG. 1 is an elevated perspective view of an exemplary occlusion clamp in accordance with the present disclosure.
Figure 2:
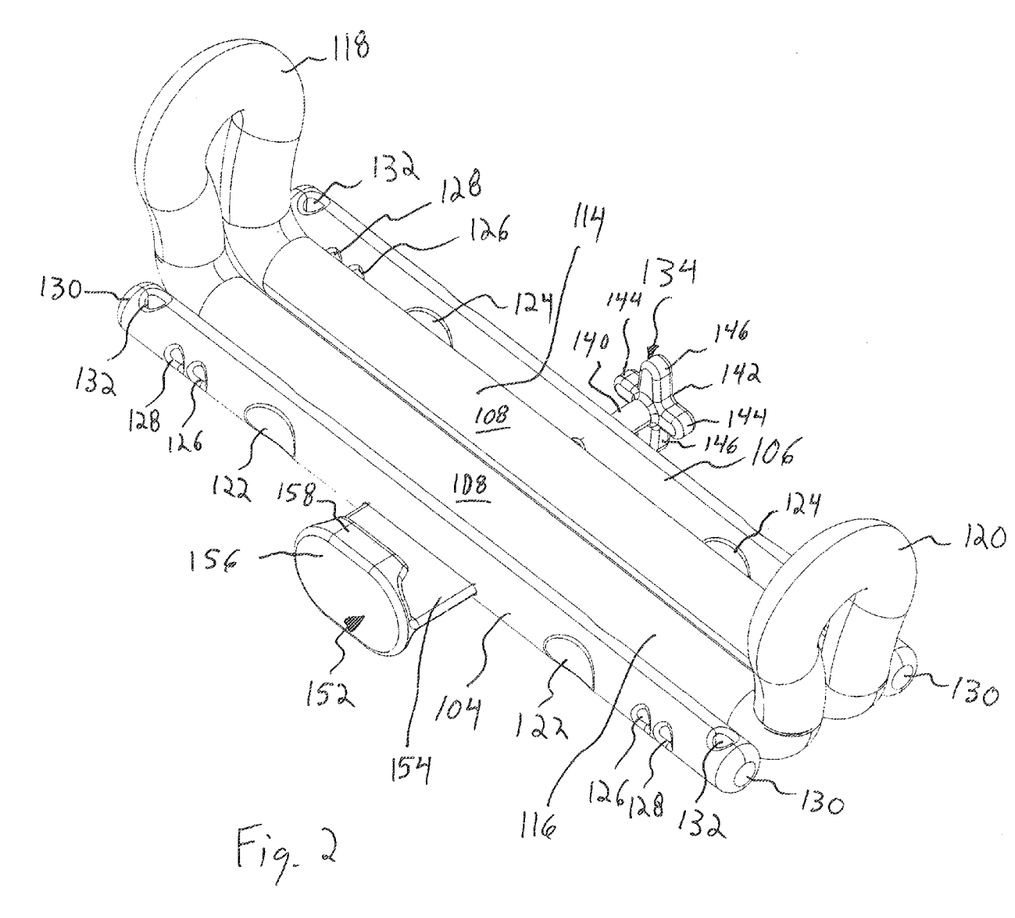
FIG. 2 is an elevated perspective view of the exemplary occlusion clamp of FIG. 1 with a pair of exemplary retainer bars.
Figure 3:
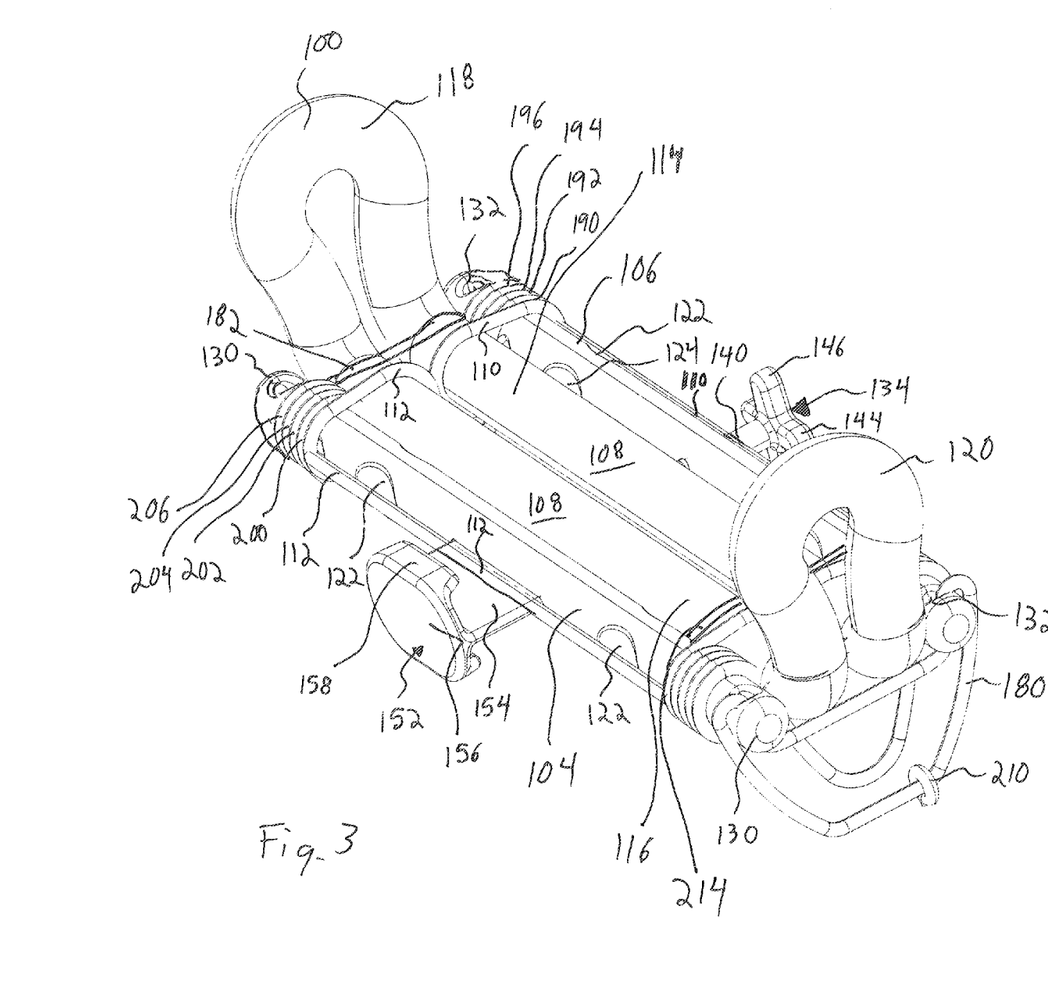
FIG. 3 is an elevated perspective view of the exemplary occlusion clamp and exemplary retainer bars of FIG. 2 being coupled together using lines.
Figure 4:
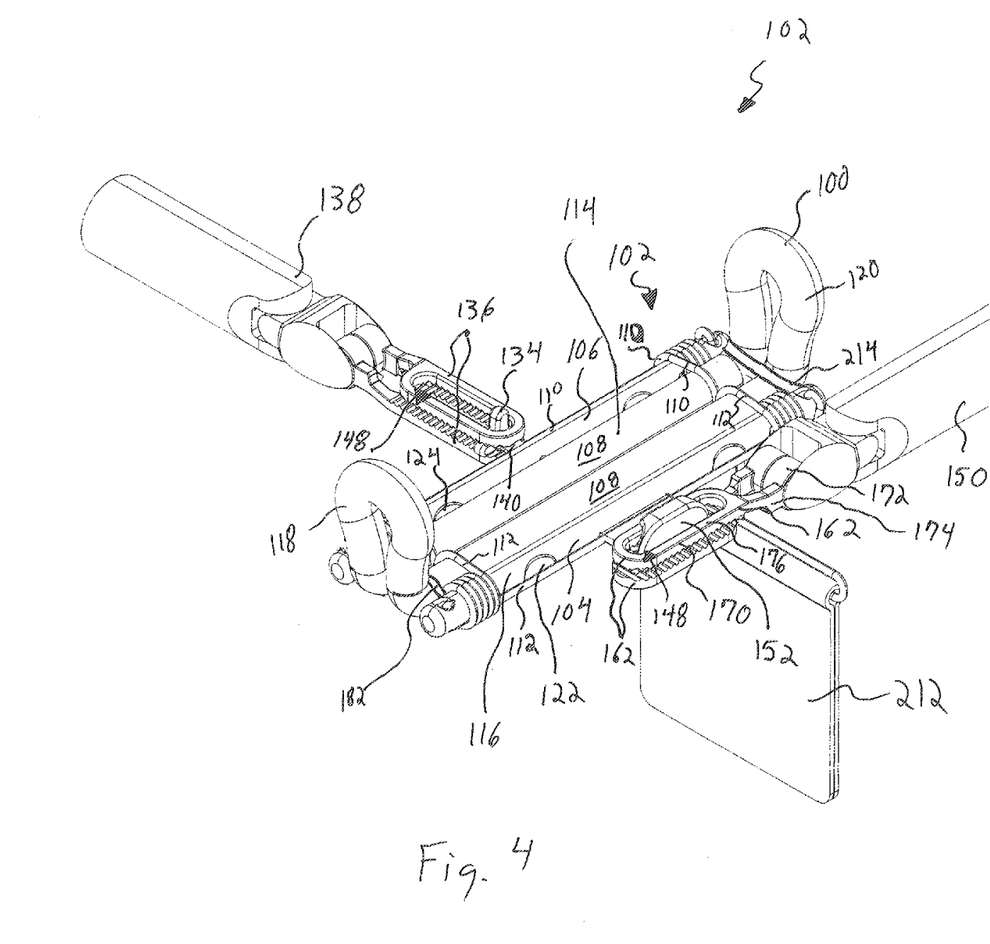
FIG. 4 is an elevated perspective view of an exemplary occlusion clamp and applicator assembly, along with a partial view of a pair of endoscopic graspers.
Figure 5:
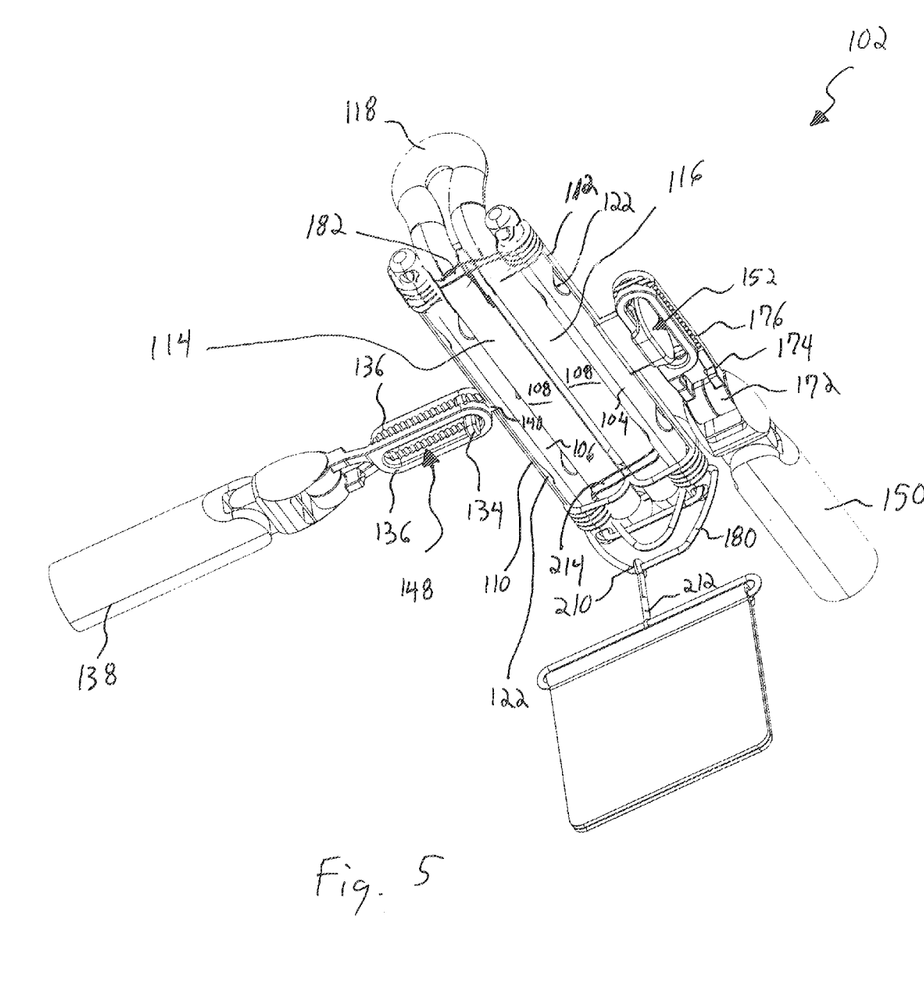
FIG. 5 is an underneath, perspective view of the exemplary occlusion clamp and applicator assembly, along with a partial view of a pair of endoscopic graspers, of FIG. 4.

While the retainer bars 104, 106 are similar, there are some distinct differences between the two. For example, the retainer bars 104, 106 need not be exact compliments or mirrors of each other. In this exemplary embodiment, the second retainer bar 106 includes a projection 134 shaped to conform to the jaws 136 of a first endoscopic grasper 138. An exemplary endoscopic grasper 138 that may be used coincident with the applicator assembly 102 includes, without limitation, the da Vinci surgical system available from Intuitive Surgical, Inc. (www.intuitivesurgical.com/products/davinci_surgicalsystem/index.aspx). This projection 134 extends perpendicularly away from the retainer bar 106 in a direction opposite the occlusion clamp 100. In this exemplary embodiment, the projection 134 extends from the same side of the retainer bar 106 as where the depressions 122 are formed. The projection 134 includes a cylindrical post 140 having mounted thereto a crucifix 142. The crucifix is oriented so that one set of coaxial projections 144 is parallel to the longitudinal axis of the retainer bar 106, while a second set of coaxial projections 146 is perpendicular to the longitudinal axis. The length of the post 140 allows the jaws 136 of the endoscopic grasper 138 to sandwich the first set of coaxial projections 144, while the second set of coaxial projections 146 extend through a respective oblong opening 148 of each endoscopic grasper 136. In particular, as shown in FIG. 4, the shape of the crucifix 142 is well suited for gripping by the jaws 136 and accommodating tension forces when the jaws 136 are repositioned to open the occlusion clamp 100 while a second endoscopic grasper 150 is coupled to the first retainer bar 104. It should also be noted that the retainer bars 104, 106 can be of varying or equivalent cross-sectional geometry.

The first retainer bar 104 may differ from the second retainer bar 106 in the shape of its projection 152. The projection 152 includes a longitudinal flange 154 having a perpendicular end plate 156 that is tapered and rounded over at its ends to form a pair of stops 158. These stops 158 generally face the longitudinal flange 154 and are oriented toward the retainer bar 104, thereby forming a pair of hooks. In other words, the projection includes a T-shaped cross-section and extends perpendicularly away from the retainer bar 104 in a generally opposite direction from the other projection 134. In this exemplary embodiment, the longitudinal flange 154 is generally rectangular in shape and is dimensioned to allow for gripping by the jaws 162 of the second endoscopic grasper 150. An exemplary endoscopic grasper 150 that may be used coincident with the applicator assembly 102 includes, without limitation, the da Vinci surgical system available from Intuitive Surgical, Inc. (www.intuitivesurgical.com/products/davinci_surgicalsystem/index.aspx).

By way of example, the jaws 136, 162 of the endoscopic graspers 138, 150 comprise a pair of individual jaws 170 pivoting around a common axis. Each jaw 170 includes a cylindrical base 172 having a bar 174 coupled to an oblong frame 176 extending perpendicularly away from the bar. The oblong frame 176 outlines the central opening 148 and is serrated on one side to facilitate gripping. As is shown in the figures, two of the jaws 170 are stacked upon one another so that the cylindrical bases 172 are aligned to be coaxial. In an exemplary configuration, the jaws 170 are oriented so that the oblong openings 148 overlap one another when the jaws 136, 162 are closed. Because of the openings 148 in the jaws 170, the jaws are able to receive portions of the projections 134, 152 and capable of exerting tensile forces against aspects of the projections in addition to possibly exerting compressive (i.e., gripping) forces on the projections.

Referring back to FIGS. 3, 4 and 5, the end plate 156 is dimensioned to extend far enough beyond the longitudinal flange 154 to accommodate the jaws 162 on opposing sides. Likewise, the height of the stops 158 and the tapered nature of the stops are dimensioned to pass into the through opening of one of the jaws 170. As will be discussed in more detail below, the jaws 162 of the second endoscopic grasper 150 grip the projection 152 and pull the projection in a direction generally opposite to the direction of the first endoscopic grasper 138 pulling on the first projection 134. This action operates to open the occlusion clamp 100.

Five distinct sutures 110, 112, 180, 182, 214 are utilized as part of the applicator assembly 102. The first suture 110 is coupled to the second retainer bar 106, while the other second suture 112 is coupled to the first retainer bar 104. In contrast, the third suture 180 is concurrently mounted to corresponding near ends of the first retainer 104 and the second retainer bar 106. The fourth suture 182 loosely circumscribes the clamping portions 114, 116 and is mounted to at least one of the clamping portions in close proximity to the urging member 118 using a subordinate suture (not shown). The fifth suture 214 also loosely circumscribes the clamping portions and is mounted to at least one of the clamping portions in close proximity to the urging member 120 using a subordinate suture (not shown). Both the fourth and fifth sutures are adapted to remain attached to the clamping portions 114, 116 post clamp 100 deployment. As will be discussed in more detail below, the third suture 180 is adapted to remain attached to the retainer bars 104, 106 in order to withdraw the retainer bars after the occlusion clamp 100 has been positioned to sandwich the appropriate tissue. Conversely, the first and second sutures are adapted to be severed to disengage the retainer bars 104, 106 from the occlusion clamp 100 post positioning. The cutting zones for severing the sutures are demarcated by the depressions 122.

In this exemplary embodiment, the manner in which the sutures 110, 112 are mounted to the retainer bars 104, 106 will now be discussed, starting with the second retainer bar 106. The second retainer bar 106 is positioned to be longitudinally parallel with the clamping portion 114 so the ends of the retainer bar are generally centered along the longitudinal length of the clamping portion 114. At the same time, the retainer bar 106 is positioned so that the projection 134 extends away from the other clamping portion 114. Likewise, the retainer bar 106 is positioned so that one opening of each of the primary through holes 126, 128 also faces toward the clamping portion 114 and the second opening of each of the primary holes faces away from the clamping portion. Finally, when the retainer bar 106 is properly positioned, the first suture 110 is concurrently attached to the retainer bar and the first clamping portion 114.

Initially, a predetermined length of suture 110 is positioned so that its midpoint is generally positioned to be on top of the cylindrical post 140 of the projection 134, with the suture being extended longitudinally to lie in parallel with the clamping portion 114. In this position, the suture 110 lies on top of the retainer bar 106 so that that suture extends across the top depressions 122. Each end of the suture 110 is then threaded through the nearest 126 of the primary holes so that the suture lies across the nearest of the two clamping portions 114, 116 (in this case, clamping portion 114). The ends of the suture 110 are then looped around the clamping portion 114 and then threaded through the farthest 128 of the primary holes and drawn taught. In this manner, the suture 110 has circumscribed the outside of the clamping portion 114. After the suture 110 is drawn taught, having been threaded through the farthest 128 of the primary holes, a first half hitch knot 190 is tied. Thereafter, a second 192 and a third 194 half hitch knots are tied in the ends of the suture 110 toward the ends of the retainer bar 106. After the three hitch knots are tied, the ends of the suture 110 are then utilized to tie a timberline knot 196, with any excess suture being removed at the end of the timberline knot. Methods of knot tying can be found in numerous resources, as can many types of knots that may be used to secure the retainer bars 104, 106 to the occlusion clamp 100 using sutures 110, 112.

An adhesive may be placed on the knots 190, 192, 194, 196 to secure the knots and eliminate or limit fraying and migration. Alternative methods of knot tying or retainer bar design may eliminate or decrease utilization of adhesives on the knots. For example, a compressive or constriction type of knot may also be used to secure the suture to the bar 104, 106. In addition, or in the alternative, heat staking or other methods of combining, lapping, and/or fixating suture-to-suture, suture-to-metal, or suture-to-plastic may be used. When the knots 190, 192, 194, 196 are completed, the suture 110 is generally taught around the retainer bar 106 and clamping portion 114 so that pulling on the retainer bar 106 away from the clamping portion 114 is operative to reposition the clamping portion 114.

The foregoing process is generally repeated for the first retainer bar 104 by positioning the retainer bar to be longitudinally parallel with the first clamping portions 116 so the ends of the retainer bar are generally centered along the longitudinal length of the clamping portion 116. At the same time, the retainer bar 104 is positioned so that the projection 152 extends away from the clamping portion 116. Likewise, the retainer bar 104 is positioned so that one opening of each of the primary through holes 126, 128 also faces toward the clamping portion 116 and a second opening of each of the primary holes faces away from the clamping portions. Finally, when the retainer bar 104 is properly positioned, the second suture 112 is attached using the following process.

Initially, a predetermined length of suture 112 is positioned so that its midpoint is generally positioned to be on top of the longitudinal flange 154 of the projection 152, with the suture being extended longitudinally to lie in parallel with the clamping portion 116. In this position, the suture 112 lies on top of the retainer bar 104 so that that suture extends across the top depressions 122. Each end of the suture 112 is then threaded through the nearest 126 of the primary holes so that the suture lies across the nearest of the two clamping portions 114, 116 (in this case, clamping portion 116). The ends of the suture 112 are then looped around the clamping portion 116 and then threaded through the farthest 128 of the primary holes and drawn taught. In this manner, the suture 112 has circumscribed the outside of the clamping portion 116. After the suture 112 is drawn taught, having been threaded through the farthest 128 of the primary holes, a first half hitch knot 200 is tied. Thereafter, a second 202 and a third 204 half hitch knots are tied in the ends of the suture 112 toward the ends of the retainer bar 104. After the three hitch knots are tied, the ends of the suture 112 are then utilized to tie a timberline knot 206, with any excess suture being removed at the end of the timberline knot. When the knots are completed, the suture 112 is generally taught around the retainer bar 104 and clamping portion 116 so that pulling on the retainer bar 104 away from the clamping portion 116 is operative to reposition the clamping portion 116.

In this exemplary embodiment, the manner in which the suture 180 is mounted to the retainer bars 104, 106 will now be discussed. The first retainer bar 104 and the second retainer bar 106 each include a secondary through hole 132 located proximate each longitudinal end. These through holes 132 are adapted to receive predetermined lengths of suture 180 in order to couple the retainer bars 104, 106 to one another. As will be discussed in more detail below, the suture 180 is not adapted to be severed, but instead remains coupled to the retainer bars 104, 106 after the sutures 110, 112 are severed to remove the retainer bars 104, 106 and remaining sutures 110, 112 attached to the retainer bars subsequent to deployment of the occlusion clamp 100.

In exemplary form, the third suture 180 is threaded through one of the secondary through holes 132 of the second retainer bar 106 so that the end of the suture extending from the opening nearest the urging member 120 is wrapped around the outside of the retainer bar 106 (and held in position) and is in proximity to the other end of the suture 180 exiting the opening facing away from the urging member 120. The end of the suture 180 exiting the opening that faces away from the urging member 120 travels across the ends of the two clamping portions 114, 116 and is threaded into the an opening of the nearest secondary through hole 132 of the first retainer bar 104, where the opening faces away from the urging member 120. When the suture 180 is threaded into this through hole 132, the end of the suture 180 travels through the hole 132 and exits nearer to the urging member 120. This free end 180 is then looped around the outside of the first retainer bar 104 and meets the other end of the suture 180 that was previously held in position to create a knot 210 to close the third suture 180, thereby forming a closed loop. In this exemplary embodiment, the third suture 180 loop is coupled to a tab 212 that provides a quickly apparent attachment point for one of the endoscopic graspers 138, 150 to grasp and withdraw the remaining sutures and retainer bars 104, 106 after the occlusion clamp 100 is deployed.

The fourth and fifth limiting lines or sutures 182, 214 are respectively loosely looped around the two clamping portions 114, 116 proximate the urging members 118, 120. A subordinate suture (not shown) is used to couple the sutures 182, 214 to the fabric cover material 108. In exemplary form, the length of the sutures 182, 214 is chosen to that when taught, the sutures operate to limit the travel of the clamping portions 114, 116. In other words, the sutures 182, 214 constrain just how far apart the clamping portions 114, 116 may be repositioned. It should be noted that the sutures may or may not be removed post occlusion clamp 100 deployment.

An exemplary deployment of the occlusion clamp 100 using the applicator assembly 102 presumes the sutures 110, 112 have been attached to the retainer bars 104, 106 as discussed above. Likewise, the exemplary deployment explanation also presumes that the sutures 180, 182, 214 have been respectively attached to the retainer bars and the clamping portions 114, 116. In exemplary form, deployment of the occlusion clamp 100 in a surgical procedure includes positioning the clamp in proximity to tissue to be clamped. Exemplary tissue that may be clamped by the occlusion clamp 100 includes, without limitation, the left atrial appendage of the heart. After the clamp 100 has been introduced proximate the tissue to be occluded, the endoscopic graspers 138, 150 are utilized to grasp the applicator assembly 102 in order to more precisely position the clamp 100.

Specifically, the jaws 136 of the first endoscopic grasper 138 are opened so that the openings 148 of each jaw overlap the coaxial projections 146 of the crucifix 142 and are thereafter shut or brought closer together to grasp the coaxial projections 144. In such an orientation, the jaws 136 of the endoscopic grasper 138 are able to pull on the crucifix 142 in a direction opposite, and coaxial with, the longitudinal direction of the cylindrical post 140. Concurrently, the jaws 162 of the second endoscopic grasper 150 are opened and oriented so that the openings 148 completely overlap the end plate 156 and stops 158. Thereafter, the jaws 162 are shut or brought closer together to grasp the longitudinal flange 154 of the projection 152. It should be noted that when the openings of the jaws 162 are oriented to completely overlap the end plate 156 and stops 158, this orientation coincides with the second endoscopic grasper 150 being oriented generally in parallel with the first retainer bar 104. After the endoscopic graspers 138, 150 have been positioned to grasp the projections 134, 152, the endoscopic graspers are repositioned to open the clamp 100.

By way of example, the second endoscopic grasper 150 may remain stationary, while the first endoscopic grasper 138 pulls on the projection 134 in a direction away from the clamp 100. This force mustered by the endoscopic graspers 138, 150 working in tandem is greater than the spring force associated with the urging members 118, 120, which results in the clamping portions 114, 116 being repositioned to create a gap therebetween. While this gap is maintained, using the relative position of the endoscopic graspers 138, 150, the clamp 100 is repositioned so that the tissue to be occluded is directed between the clamping portions 114, 116. After the tissue is placed between the clamping portions 114, 116 to the satisfaction of the surgeon, the endoscopic graspers 138 are repositioned toward one another so that the spring force of the clamping portions 114, 116 is applied to the tissue in question. Thereafter, surgical snips (not shown) are introduced, while the clamp 100 is positioned to clamp the tissue in question, to sever the sutures 110, 112. Specifically, the snips are introduced proximate the depressions 122 on each of the retainer has 104, 106 to sever the sutures 110, 112, thereby creating a new pair of free ends for each suture. But it should be noted that the sutures 180 remain, thereby linking the retainer bars 104, 106 to one another. It is the new free ends of the sutures 110, 112 that discontinue the sutures being taught and the coupling between the retainer bars 104, 106 and the clamping portions 114, 116. In this manner, a surgeon grasps the tab 212 and pulls the retainer bars 104, 106 from the surgical region and the clamp 300. Because the tab 212 remains attached to the retainer bars 104, 106 by way of the suture 180, and because the sutures 110, 112 remain attached to the retainer bars by way of the knots 190, 192, 194, 196, 200, 202, 204, 206, pulling on the tab 212 removes concurrently removes the retainer bars and the sutures. In exemplary form, the tab 212 is adapted to be positioned at all times outside of the body cavity.

The foregoing components may be fabricated from any surgical grade material. By way of example, the retainer bars 104, 106 are fabricated from a metal, such as stainless steel, aluminum, or titanium, while the sutures can be obtained commercially available from Ethicon (J&J) or fabricated for use. Whilst not necessary to use adhesive on the knots, a person skilled in knot tying may create a compressive or constrictive type of knot in order to eliminate or reduce the amount of adhesive. Adhesives for use with the foregoing exemplary embodiments may include CA, UV-CA, or other medical or non-medical grade adhesives. The projections can be of similar geometry or differing geometries. The retainer bars 104, 106 can be of varying or equivalent cross-sectional geometries.

Following from the above description and invention summaries, it should be apparent to those of ordinary skill in the art that, while the methods and apparatuses herein described constitute exemplary embodiments of the present invention, the invention contained herein is not limited to this precise embodiment and that changes may be made to such embodiments without departing from the scope of the invention as defined by the claims. Additionally, it is to be understood that the invention is defined by the claims and it is not intended that any limitations or elements describing the exemplary embodiments set forth herein are to be incorporated into the interpretation of any claim element unless such limitation or element is explicitly stated. Likewise, it is to be understood that it is not necessary to meet any or all of the identified advantages or objects of the invention disclosed herein in order to fall within the scope of any claims, since the invention is defined by the claims and since inherent and/or unforeseen advantages of the present invention may exist even though they may not have been explicitly discussed herein.

What is claimed is:

1. A clamp assembly comprising:
a clamping device biased toward a closed position;
a first retainer bar removably coupled to the clamping device;
a second retainer bar removably coupled to the clamping device; and,
wherein the first retainer bar and the second retainer bar are oriented in parallel to one another; and, wherein at least one of the first retainer bar and the second retainer bar is removably coupled to the clamping device using a suture; and,
wherein the first retainer bar and the second retainer bar each include an engagement feature to facilitate grasping by a grasping device.

2. The clamp assembly of claim 1, wherein the first retainer bar includes a projection extending therefrom, the projection including a crucifix.

3. The clamp assembly of claim 1, wherein the second retainer bar includes a projection extending therefrom, the projection including a first segment extending perpendicularly from the second retainer bar, and a second segment including a hook mounted to the first segment.

4. The clamp assembly of claim 1, wherein:
the first retainer bar includes a first projection adapted to he gripped by manual endoscopic graspers, where the first projection is directed away from the clamp; and,
the second retainer bar includes a second projection adapted tube gripped by manual endoscopic graspers, where the second projection is directed away from the clamp.

5. The clamp assembly of claim 1, wherein:
the first retainer bar includes a first projection adapted to be gripped by robotically driven endoscopic graspers, where the first projection is directed away from the clamp; and,
the second retainer bar includes a second projection adapted to be gripped by robotically driven endoscopic graspers, where the second projection is directed away from the clamp.

6. The clamp assembly of claim 1, wherein
the first retainer bar is removably coupled to the clamping device using a first suture; and,
the second retainer bar is removably coupled to the clamping device using a second suture.

7. A clamp assembly comprising:
a clamp including at least first and second elongate clamping portions biased toward one another;
a first retainer bar including a first line removably coupling the first retainer bar to the first elongate clamping portion; and,
a second retainer bar including a second line removably coupling the second retainer bar to the second elongate clamping portion;
wherein the first retainer bar is coupled to the second retainer bar.

8. The clamp assembly of claim 7, wherein the first retainer bar includes a projection extending therefrom, the projection including a crucifix.

9. The clamp assembly of claim 7, wherein the second retainer bar includes a projection extending therefrom, the projection including a first segment extending perpendicularly from the second retainer bar, and a second segment including a hook mounted to the first segment.

10. The clamp assembly of claim 7, wherein the second retainer bar includes a projection extending therefrom, the projection including a hook.

11. The clamp assembly of claim 7, wherein:
the first retainer bar includes a first through hole;
the second retainer bar includes a second through hole; and,
the third line is concurrently received within the first through hole and the second through hole.

12. The clamp assembly of claim 11, further comprising an extraction tab coupled to the third line.

13. The clamp assembly of claim 7, wherein at least one of the first line, the second line, and the third line comprises a suture.

14. A method of fabricating a clamp comprising:
mounting a first retainer bar to a first elongate clamping portion of a clamp, the clamp also including a second elongate clamping potion, where the first and second elongate clamping portions are biased toward one another;
mounting a second retainer bar to the second elongate clamping portion of the clamp; and,
wherein the first and second elongate clamping portions each include proximal and distal longitudinal ends;
wherein the proximal longitudinal ends are coupled to a first spring; and,
wherein the distal longitudinal ends arc coupled to a second spring.

15. A clamp assembly comprising:
a clamping device biased toward a closed position;
a first retainer bar removably coupled to the clamping device;
a second retainer bar removably coupled to the clamping device; and, wherein the first retainer bar and the second retainer bar are oriented in parallel to one another; and, wherein at least one of the first retainer bar and the second retainer bar is removably coupled to the clamping device using a suture.

* * * * *